United States Patent [19]

Lawrence

[11] 4,234,470

[45] Nov. 18, 1980

[54] CATALYTIC NITRATION OF AROMATIC COMPOUNDS

[75] Inventor: Frederick R. Lawrence, Claymont, Del.

[73] Assignee: E. I. Du Pont de Nemours and Company, Wilmington, Del.

[21] Appl. No.: 32,346

[22] Filed: Apr. 23, 1979

[51] Int. Cl.³ .............................................. C07C 79/10
[52] U.S. Cl. .................................. 568/939; 260/365; 564/411; 568/929; 568/937; 568/938; 568/940
[58] Field of Search ................ 260/365, 578, 645, 646

[56] References Cited

U.S. PATENT DOCUMENTS

| | | | |
|---|---|---|---|
| 2,948,759 | 8/1960 | Wright | 260/645 X |
| 3,196,186 | 7/1965 | Sogn et al. | 260/645 |
| 3,965,200 | 6/1976 | Manabe et al. | 260/645 |

FOREIGN PATENT DOCUMENTS 50-154212  12/1975  Japan .

*Primary Examiner*—Leland A. Sebastian

[57] ABSTRACT

A process for the continuous catalytic vapor-phase mononitration of aromatic compounds, especially benzene, using as the catalyst an α-fluorosulfonic acid polymer admixed with a complement inert to the nitration reaction and dimensionally stable under the reaction conditions.

9 Claims, No Drawings

CATALYTIC NITRATION OF AROMATIC COMPOUNDS

DESCRIPTION

1. Technical Field

This invention relates to a process for the nitration of aromatic compounds. It is more particularly directed to a process for the continuous catalytic vapor-phase nitration of aromatic compounds using as the catalyst a particulate α-fluorosulfonic acid polymer that has been admixed with a complement which is inert to the nitration reaction and dimensionally stable under the conditions of nitration.

2. BACKGROUND ART

It is known to catalytically nitrate aromatic compounds such as benzene in the vapor phase, using a particulate α-fluorosulfonic acid polymer as the catalyst. This is shown in Japanese Patent Application 50-154212, published on Dec. 12, 1975. When operated under proper conditions, a process of the type shown there is superior to the mixed acid process customarily used because it avoids the inherent problem of reconstituting the sulfuric acid portion of the nitrating agent. It has been found, however, that when such a process is used in a fixed catalyst bed continuous vapor-phase operation, the α-fluorosulfonic acid polymer particles become fused after a short time and the nitration reaction either stops or slows to the point of commercial uselessness.

A need therefore exists for a process using an α-fluorosulfonic acid polymer as the catalyst, but in which the polymer remains in particulate form as the nitration reaction proceeds.

DISCLOSURE OF THE INVENTION

This need is filled by the process of the present invention, in which a particulate α-fluorosulfonic acid polymer catalyst is used in admixture with a particulate complement, inert to the nitration reaction and dimensionally stable under the reaction conditions. The process of the invention not only minimizes fusion of the catalyst in the system, but also allows the nitration to give improved yields by minimizing formation of undesirable polynitro aromatic compounds.

While the benefits of the process of the invention are greatest in the mononitration of benzene, the process can also be used in the mononitration of other aromatic compounds such as chlorobenzene, dichlorobenzene, toluene, naphthalene, anthracene, toluidine and anthraquinone.

The nitrating agent used in the process of the invention is ordinarily and preferably nitric acid, in any of the commercial strengths of 55-68.4%. Oxides of nitrogen, preferably $NO_2$, can also be used, as well as mixtures of nitrating agents.

The catalyst used in the process of the invention is a polymer bearing α-fluorosulfonic acid groups, referred to herein as "an α-fluorosulfonic acid polymer."

"α-Fluorosulfonic acid" describes a compound in which at least one fluorine atom is attached to the carbon atom in the alpha position to the —$SO_3H$ group of the acid.

Illustrative of such catalyst polymers are α-fluorosulfonic acid polymers which are homopolymers of ethylenically unsaturated monomers (a) containing groups such that the final polymers will contain groups of the formula

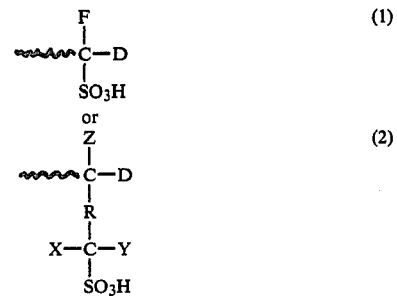

where ⁓ represents the polymer chain or a segment thereof;

D is hydrogen, an aliphatic or aromatic hydrocarbon radical of 1–10 carbon atoms, halogen or a segment of the polymer chain;

X and Y are hydrogen, halogen or an aliphatic or aromatic hydrocarbon radical of 1–10 carbon atoms, but at least one of X or Y must be fluorine;

R is a linear or branched linking group having up to 40 carbon atoms in the principal chain; and Z is hydrogen, halogen or an aliphatic or aromatic hydrocarbon radical of 1–10 carbon atoms;

or copolymers of monomers (a) with other copolymerizable ethylenically unsaturated monomers (b).

The linking group defined by R in formula (2) can be a homogeneous one such as an alkylene radical, or it can be a heterogeneous one such as an alkylene ether radical. In the preferred catalysts, this linking radical contains 1–20 carbon atoms in the principal chain. In the especially preferred catalyst, R is a radical of the structure

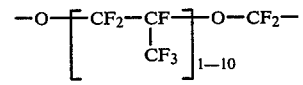

Illustrative of monomer (a) are such monomers as trifluorovinyl sulfonic acid, linear or branched chain vinyl monomers containing sulfonic acid group precursors and perfluoroalkylvinyl ethers containing sulfonic acid group precursors.

Illustrative of monomer (b) are such monomers as ethylene, styrene, vinyl chloride, vinyl fluoride, vinylidene fluoride, chlorotrifluoroethylene (CTFE), bromotrifluoroethylene (BTFE), vinyl ethers, perfluoroalkyl vinyl ethers, butadiene, tetrafluoroethylene (TFE) and hexafluoropropylene (HFP).

The homopolymerization and copolymerization can be done according to the procedures described in U.S. Pat. No. 3,784,399 to Grot, and the patents cited therein. Monomer ratios are selected to give the resulting polymer the proper equivalent weight.

The catalysts have equivalent weights of 950–1,500, preferably 1,100–1,300. Equivalent weight of a catalyst is that weight in grams which contains one gram equivalent weight of sulfonic acid groups, and can be determined by titration.

The catalyst should be effectively free of functional groups, other than —$SO_3H$ groups, which might interfere with the nitration reaction. "Effectively free" means the catalyst may contain a small number of such groups, but not so many that the nitration reaction is affected adversely or the product contaminated. Illustrative of such groups are carboxyl groups, hydroxyl groups and amino groups.

Catalysts whose polymer chains are of perfluorocarbon monomers are preferred for use in the process of the invention. Illustrative of such monomers are TFE, HFP, CTFE, BTFE and perfluoroalkyl vinyl ethers. Mixtures of monomers can also be used.

Even more preferred as catalysts are copolymers of TFE or CTFE and a perfluoroalkyl vinyl ether containing sulfonic acid group precursors. Most preferred in this class are copolymers of TFE or CTFE and a monomer represented by the structure

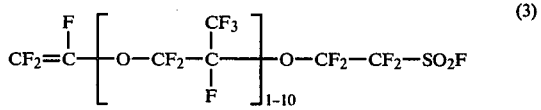

(3)

These copolymers are prepared in the sulfonyl fluoride form and are then hydrolyzed to the acid form as described in U.S. Pat. No. 3,692,569.

Most preferred as catalysts are copolymers of TFE and monomers of formula (3) in which the respective monomer unit weight ratios are 50-75/25-50. Such copolymers, having equivalent weights of 1100, 1150, 1200 and 1500, are sold by E. I. du Pont de Nemours and Company as Nafion ® perfluorosulfonic acid resins.

The catalyst used in the process is particulate. Particle size is a matter of choice, governed by the activity of the catalyst itself, the rate of nitration desired, the nitrating agent used, and like factors. In general, nitration proceeds best when the catalyst particles are of such size that they pass through a U.S.S. No. 6 sieve (−U.S.S. 6) but are retained on a U.S.S. No. 100 sieve (+U.S.S. 100), preferably U.S.S. −20 and U.S.S. +50.

The complement with which the catalyst is admixed before it is used must meet three criteria: it must be particulate, it must be inert to the nitration reaction and must be dimensionally stable under the reaction conditions, i.e., it must not flow or fuse during the reaction. Illustrative of materials which can be used are refractory materials such as silicon carbide, alumina, silica and zirconia and glasses and sands. Organic polymeric materials which resist degradation and deformation at high temperatures, such as polytetrafluoroethylene, can also be used. Silicon carbide is preferred for use because of its excellent high temperature properties and its availability. Mixtures of complements can also be used.

To obtain the full benefit of the invention, the complement particle size should be −U.S.S. 3½ to about +U.S.S. 325. In a preferred embodiment, the catalyst particles and complement particles are as nearly the same in size as is practical.

The catalyst and complement are admixed before use in such proportions that the final mixture contains at least about 10%, by volume, of complement. The upper limit of complement content is a practical one; quite obviously, if too much is present the catalyst will be diluted to the point at which the rate of nitration becomes unacceptable. In general, mixtures containing as much as 80%, by volume, of complement perform satisfactorily. Preferred for use, especially in the mononitration of benzene, are mixtures in which the catalyst/complement volume ratio is 40/60-60/40. Even more preferred are the 40/60 mixtures.

The catalyst/complement mixtures are prepared by charging the catalyst and complement to a container, in any order, and then slowly tumbling the container for 5-10 minutes.

The resulting mixture is packed into a suitable fixed-bed reactor, where it is held in place by means of suitable screens or baffles.

The aromatic compound to be nitrated and the nitrating agent are then fed into the catalyst bed in such a way that they come in contact with the catalyst in the vapor phase. This can be done by mixing the aromatic compound and nitrating agent, vaporizing the mixture by suitable means and then feeding the vapors to the bed. Alternatively, it can be accomplished by separately vaporizing the aromatic compound and the nitrating agent, mixing the vapors and then feeding the mixture to the catalyst bed.

In a preferred embodiment, liquid aromatic compound and liquid nitrating agent are separately fed to a preheater, where they are mixed and warmed to about 80°-120° C. The warmed mixture is then fed to the catalyst bed, where the heat of the nitration reaction vaporizes it. In a variation of this procedure, the liquid reactants are first mixed and the mixture preheated and then fed to the catalyst bed.

However the aromatic compound and nitrating agent are brought to the catalyst bed, they will be present in nitrating agent/aromatic compound molar ratios of 0.1-10/1.0, preferably 0.2-2.0/1.0. The actual ratio used for any given nitration will be governed by the nature of the aromatic compound and of the nitrating agent, and the conditions of reaction, as will be understood by those skilled in this art.

During the nitration reaction, the catalyst bed is at an average temperature of about 100° C. to somewhat below the degradation temperature of the catalyst used. In general, the temperature is in the range of 115°-180° C., preferably 135°-155° C. Average bed temperature is calculated from temperatures taken at 2.54 cm (1 inch) intervals in a thermowell set in the center of the bed. Since the nitration reaction is exothermic, temperatures are ordinarily held within the desired range by suitable cooling means, or in an adiabatic system, by controlling the temperature of the preheater or the composition of the reactant feed.

The aromatic compound and nitrating agent are continuously passed through the catalyst bed at a superficial space velocity of 0.5-5.0 milliliters of liquid feed per hour per cubic centimeter of catalyst-complement mixture, preferably 1-2 milliliters per hour.

The effluent from the bed contains the nitrated aromatic compounds, unreacted nitric acid or oxides of nitrogen, unreacted aromatic compound, water of reaction and byproduct polynitro aromatic compounds. The effluent separates into an organic phase containing the nitrated aromatic compounds, the unreacted aromatic compound and the byproducts, and an acid phase containing acid and water. These phases can be separated by decantation. Unreacted acid can be reconstituted and recycled if desired. The nitrated aromatic compound and unreacted aromatic compound can be separated from the organic phase by conventional engineering techniques, and the unreacted portion can also be recycled if desired.

EXAMPLES

The procedures described in the following examples were carried out in a quartz reactor 50.8 cm long, with an inside diameter of 2.54 cm and an outside diameter of 3.2 cm. Separate quartz jackets were provided for the top preheater section (28 cm of the total reactor length) and the bottom catalyst section (22.8 cm). Silicon oil from two constant temperature baths was fed to the jackets for heat control. The preheater section was filled with glass split rings 0.7 cm outside diameter, 0.48 cm inside diameter.

Nitric acid and the aromatic compound were separately fed into the reactor and admixed in a downward direction in the preheater section at 80°–120° C.

The catalyst section was charged with catalyst and complement, as described.

In each procedure, the catalyst particles showed no evidence of fusion after 30 hours of continuous use.

| Example | Catalyst and Complement | Amount Volume | HNO$_3$ 65% | Feed-Parts/Feed-Parts/Volume/-Hour | | |
|---|---|---|---|---|---|---|
| | | | | Benzene | Chlorobenzene | Toluene |
| 1 (Best Mode) | Nafion®H 501 −20 +50 | 41 pts | 38 | 124 | — | — |
| | Silicon carbide −20 +50 | 58.5 pts | | | | |
| 2 | Nafion®H −8 +12 | 75 pts | 60 | 90 | — | — |
| | Teflon® TFE fluorocarbon resin −8 +12 | 25 pts | | | | |
| 3 | Nafion®H 511 −20 +50 | 61 pts | 48 | 66 | — | — |
| | Ground quartz −20 +50 | 61 pts | | | | |
| 4 | Nafion®H −16 +60 | 61 pts | 52 | — | 90 | — |
| | Silicon carbide −16 +60 | 61 pts | | | | |
| 5 | Nafion®H −16 +60 | 61 pts | 55.5 | — | — | 83.3 |
| | Silicon carbide −16 +60 | 61 pts | | | | |

| Example | Feed Molar Ratio HNO$_3$/Aromatic Compound | Superficial Space Velocity | Average Catalyst Bed Temperature °C. |
|---|---|---|---|
| 1 | 0.39/1 | 1.62 | 147° |
| 2 | 0.85/1 | 1.50 | 132° |
| 3 | 0.93/1 | 0.93 | 144° |
| 4 | 0.85/1 | 1.16 | 143.8° |
| 5 | 1.02/1 | 1.14 | 118° |

INDUSTRIAL APPLICABILITY

The process of the invention can be used to mononitrate benzene to form mononitrobenzene, a commodity in the chemical industry, widely used as an intermediate in the preparation of aniline.

I claim:

1. In the process for the continuous catalytic vapor-phase mononitration of an aromatic compound, in which the aromatic compound, a nitrating agent and a particulate α-fluorosulfonic acid polymer catalyst are brought together under conditions suitable for nitration, the improvement which comprises admixing the catalyst, before it is used, with at least 10%, by volume of the catalyst, of a particulate complement, inert to the nitration reaction, dimensionally stable under the reaction conditions, and having a particle size of −U.S.S. 3½ +U.S.S. 325.

2. The process of claim 1 wherein the catalyst has a particle size of −U.S.S. 6+U.S.S. 100.

3. The process of claim 2 wherein the complement material has a particle size of −U.S.S. 6 +U.S.S. 100.

4. The process of claim 1 wherein the complement is a refractory material.

5. The process of claim 1 wherein the complement is silicon carbide, silica, a glass, sand or polytetrafluoroethylene.

6. The process of claim 3 wherein the complement is silicon carbide.

7. A process for the continuous catalytic vapor-phase mononitration of benzene, the process comprising bringing together, under conditions suitable for nitration, benzene, nitric acid and a physical mixture of
   (1) a particulate catalyst having a particle size of −U.S.S. 6 +U.S.S. 100, the catalyst being a homopolymer of an ethylenically unsaturated monomer
       (a) containing groups such that the final polymer will contain groups of the formula

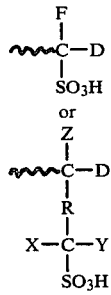

where ∿ represent the polymer chain or a segment thereof;

D is hydrogen, an aliphatic or aromatic hydrocarbon radical of 1–10 carbon atoms, halogen or a segment of the polymer chain;

X and Y are hydrogen, halogen or an aliphatic or aromatic hydrocarbon radical of 1–10 carbon atoms, but at least one of X or Y must be fluorine;

R is a linear or branched linking group having up to 40 carbon atoms in the principal chain; and Z is hydrogen, halogen or an aliphatic or aromatic hydrocarbon radical of 1–10 carbon atoms;

or a copolymer of monomer (a) with at least one other copolymerizable ethylenically unsaturated monomer (b), the homopolymer or copolymer having an equivalent weight of 950–1500; and (2) a particulate complement, inert to the nitration reaction, dimensionally stable under the reaction conditions and having a particle size of −U.S.S. 3½ +U.S.S. 325.

8. The process of claim 7 wherein the catalyst is a hydrolyzed copolymer of TFE or CTFE and a monomer represented by the structure
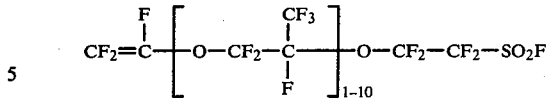
9. The process of claim 8 wherein the complement is silicon carbide having a particle size of −U.S.S. 6 +U.S.S. 100.